(12) United States Patent
Khurana

(10) Patent No.: US 9,615,934 B2
(45) Date of Patent: Apr. 11, 2017

(54) PROTECTIVE COVER FOR INTERBODY FUSION DEVICES

(71) Applicant: Sanjay K. Khurana, Marina Del Rey, CA (US)

(72) Inventor: Sanjay K. Khurana, Marina Del Rey, CA (US)

( * ) Notice: Subject to any disclaimer, the term of this patent is extended or adjusted under 35 U.S.C. 154(b) by 0 days.

(21) Appl. No.: 13/857,747

(22) Filed: Apr. 5, 2013

(65) Prior Publication Data

US 2013/0297024 A1 Nov. 7, 2013

Related U.S. Application Data

(60) Provisional application No. 61/621,041, filed on Apr. 6, 2012.

(51) Int. Cl.
| | |
|---|---|
| *A61F 2/44* | (2006.01) |
| *A61F 2/30* | (2006.01) |
| *A61F 2/46* | (2006.01) |
| *A61F 2/28* | (2006.01) |

(52) U.S. Cl.
CPC .......... *A61F 2/441* (2013.01); *A61F 2/30744* (2013.01); *A61F 2/447* (2013.01); *A61F 2/30723* (2013.01); *A61F 2/4611* (2013.01); *A61F 2002/2817* (2013.01); *A61F 2002/2835* (2013.01); *A61F 2002/305* (2013.01); *A61F 2002/30143* (2013.01); *A61F 2002/30172* (2013.01); *A61F 2002/30197* (2013.01); *A61F 2002/30507* (2013.01); *A61F 2002/30774* (2013.01); *A61F 2002/4475* (2013.01)

(58) Field of Classification Search
CPC .......... A61F 2/44–2/447; A61F 2/4601; A61F 2/4455; A61F 2/4611; A61F 2002/2817; A61F 2002/2835; A61F 2002/4475
USPC ............................................ 623/17.11–17.16
See application file for complete search history.

(56) References Cited

U.S. PATENT DOCUMENTS

| | | | | |
|---|---|---|---|---|
| 5,888,223 | A * | 3/1999 | Bray, Jr. ..................... | 623/17.16 |
| 6,391,058 | B1 * | 5/2002 | Kuslich ................. | A61F 2/4455 |
| | | | | 623/17.11 |
| 7,837,735 | B2 | 11/2010 | Malone | |
| 8,142,503 | B2 | 3/2012 | Malone | |
| 2002/0169507 | A1 | 11/2002 | Malone | |
| 2004/0225360 | A1 | 11/2004 | Malone | |
| 2005/0038512 | A1 * | 2/2005 | Michelson ................ | 623/17.11 |
| 2005/0159813 | A1 * | 7/2005 | Molz ......................... | 623/17.11 |
| 2007/0083265 | A1 | 4/2007 | Malone | |
| 2007/0255416 | A1 * | 11/2007 | Melkent et al. ........... | 623/17.16 |
| 2007/0270963 | A1 * | 11/2007 | Melkent et al. ........... | 623/17.11 |
| 2007/0282446 | A1 * | 12/2007 | Li .......................... | A61B 17/68 |
| | | | | 623/17.12 |
| 2008/0051890 | A1 * | 2/2008 | Waugh et al. ............. | 623/17.11 |
| 2008/0249569 | A1 * | 10/2008 | Waugh ................ | A61F 2/30721 |
| | | | | 606/249 |

(Continued)

*Primary Examiner* — Eduardo C Robert
*Assistant Examiner* — Michelle C Eckman
(74) *Attorney, Agent, or Firm* — MH2 Technology Law Group LLP

(57) ABSTRACT

A protective cover prevents undesired leakage of materials out of a spinal implant. In one embodiment, the implant is a lateral interbody fusion implant that accommodates biologically active material to promote bone ingrowth. The protective cover prevents unintended migration of the biologically active material out of the implant and into surrounding tissue.

9 Claims, 2 Drawing Sheets

(56) References Cited

U.S. PATENT DOCUMENTS

| | | |
|---|---|---|
| 2009/0182430 A1* | 7/2009 | Tyber et al. ............... 623/17.16 |
| 2009/0198339 A1* | 8/2009 | Kleiner et al. ............. 623/17.16 |
| 2009/0234455 A1* | 9/2009 | Moskowitz et al. ....... 623/17.11 |
| 2010/0145459 A1* | 6/2010 | McDonough et al. .... 623/17.16 |
| 2011/0029081 A1 | 2/2011 | Malone |
| 2012/0065734 A1* | 3/2012 | Barrett ................. A61F 2/4455 623/17.16 |
| 2012/0078373 A1* | 3/2012 | Gamache et al. ......... 623/17.16 |
| 2012/0165871 A1 | 6/2012 | Malone |
| 2012/0245690 A1* | 9/2012 | Cowan et al. ............. 623/17.16 |
| 2013/0345814 A1* | 12/2013 | Walkenhorst et al. .... 623/17.16 |
| 2014/0135930 A1* | 5/2014 | Georges .................... 623/17.16 |

* cited by examiner

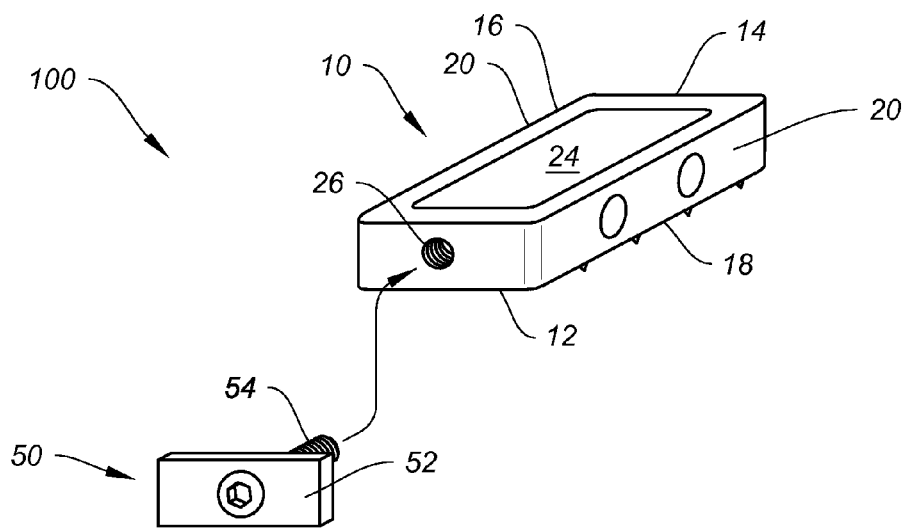
FIG. 1
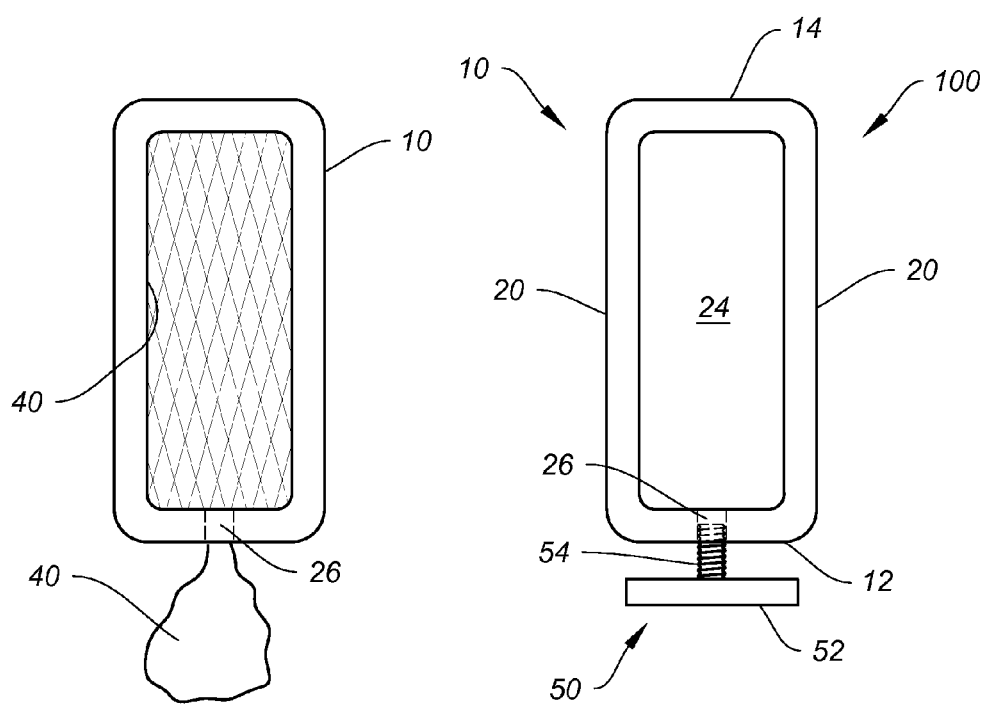
FIG. 2A
FIG. 2B

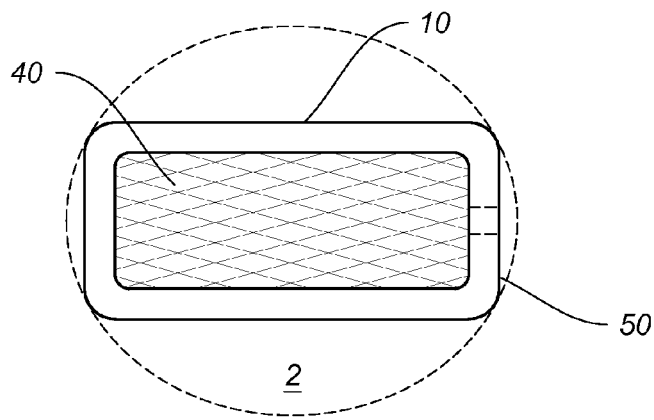
FIG. 3A
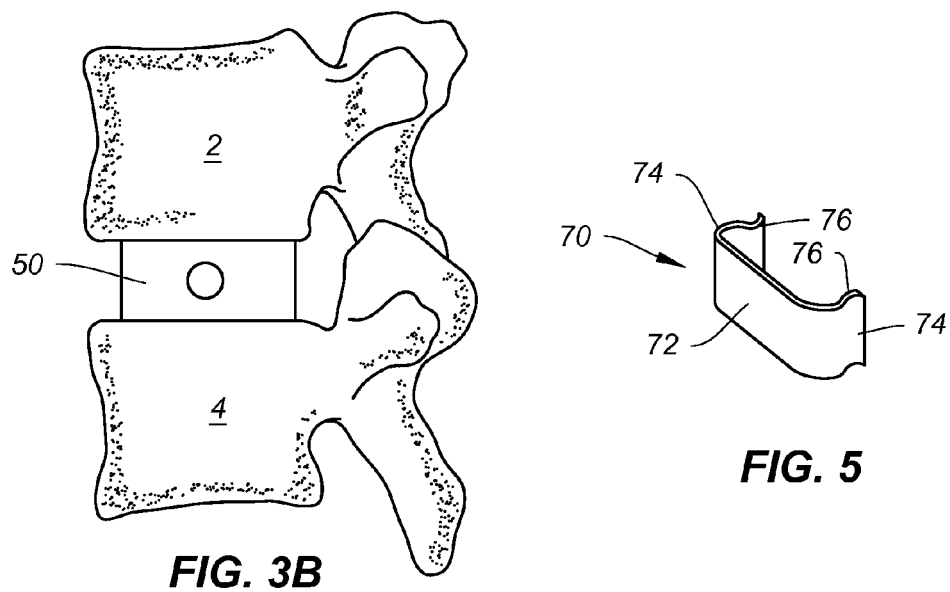
FIG. 3B
FIG. 5
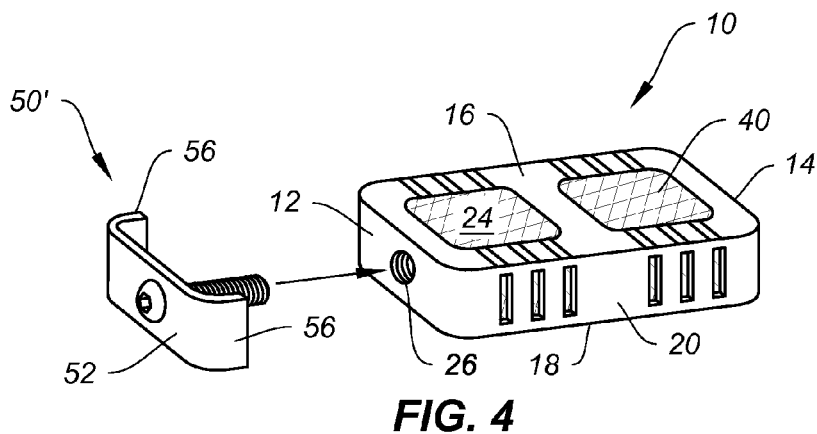
FIG. 4

PROTECTIVE COVER FOR INTERBODY FUSION DEVICES

CROSS-REFERENCE TO RELATED APPLICATIONS

This application claims priority to U.S. Provisional No. 61/621,041 filed Apr. 6, 2012 and entitled "Protective Cover for Interbody Fusion Devices," the contents of which are herein incorporated in their entirety by reference.

FIELD

The present invention relates to a medical device, and more particularly to an accessory for implantable interbody fusion devices. Even more particularly, the present invention relates to a protective cover for implantable interbody fusion devices.

BACKGROUND

A conventional method of spine repair involves immobilizing weakened, damaged or diseased segments of the vertebrae by attaching a fusion-promoting implant or prosthesis to adjacent vertebral bodies. These fusion-promoting implants may be inserted laterally, and configured to hold a biologically active material to enhance bone ingrowth. The implants are typically manipulated and delivered with an instrument system that engages the implant using one or more delivery tools attached to a tool engaging hole. Once deployed, however, the tool engaging hole is typically left open or exposed. This allows the potential for undesired leakage of material out of the implant into surrounding tissue. For example, when used with a biologically active material such as a recombinant bone morphogenic protein, biologic molecules may leak into the surrounding iliopsoas muscle and cause inflammation, numbness, pain, weakness, flexion contractures, etc.

Accordingly, it would be desirable to provide an accessory that can be used with these types of fusion implant devices and biologically active materials to prevent such migration of material out of the devices and into the surrounding tissues. It would be even more desirable to provide such an accessory having ease of use, and compatibility with a variety of known and currently available fusion implants.

SUMMARY

The present disclosure provides protective covers that can be used with many different types of implantable interbody fusion devices and biologically active materials to prevent such migration of material out of the devices and into the surrounding tissues. These protective covers are easy to use, do not require specialized tools for insertion, and are compatible with a variety of known and currently available interbody fusion devices.

One embodiment provides an instrument system comprising: a lateral interbody device comprising a first end, a second end, upper and lower surfaces for placement against vertebral bodies, a pair of sidewalls extending between the upper and lower surfaces and connecting the first end and second end, at least one cavity between the upper and lower surfaces configured to hold a biologic material that facilitates bony ingrowth between adjacent vertebral bodies, and a tool engaging opening; and a protective cover configured to prevent leakage of the biologic material from the cavity, wherein the protective cover comprises a plate and at least one stem configured for attachment to the tool engaging opening.

Another embodiment provides a protective cover for a lateral interbody fusion device, wherein the cover is configured to prevent leakage of biologic material from the fusion device. The cover may comprise a plate having a profile configured to mate with an outer surface of the lateral interbody fusion device and at least one stem configured for attachment to a tool engaging opening of the lateral interbody fusion device.

Still another embodiment provides a protective cover for a lateral interbody fusion device, wherein the cover is configured to prevent leakage of biologic material from the fusion device. The cover may comprise a main body having a plate-like profile configured to mate with an outer surface of the lateral interbody fusion device. The cover may further comprise a pair of sidewalls extending into clips configured to snap onto the lateral interbody fusion device.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

FIG. 1 shows an exploded view of an exemplary embodiment of an implantable system of the present disclosure.

FIG. 2A shows a top plan view of an implant without an exemplary embodiment of a protective cover of the present disclosure.

FIG. 2B shows a top plan exploded view of an implant with an exemplary embodiment of a protective cover of the present disclosure.

FIG. 3A shows a top plan view of an implant and protective cover in situ within a patient's body.

FIG. 3B shows a side view of an implant and protective cover in situ within a patient's body.

FIG. 4 shows an exploded view of another exemplary embodiment of an implantable system of the present disclosure.

FIG. 5 shows a perspective view of still another exemplary embodiment of a protective cover of the present disclosure.

DESCRIPTION OF THE EMBODIMENTS

The embodiments provide a protective cover for preventing undesired leakage of materials out of a spinal implant. In one embodiment, the implant is a lateral interbody fusion implant that accommodates biologically active material to promote bone ingrowth. The protective cover prevents unintended migration of the biologically active material out of the implant and into surrounding tissue.

Reference will now be made to the figures to illustrate various aspects and embodiments of the present invention. In the following detailed description, numerous specific details are set forth to provide a full understanding of the present invention. It will be apparent, however, to one ordinarily skilled in the art that the present invention may be practiced without some of these specific details. In other instances, well-known structures and techniques have not been shown in detail to avoid unnecessarily obscuring the present invention.

FIG. 1 shows an exploded view of an implantable system 100. As shown, an interbody device 10 comprises first end 12 and second end 14 and upper and lower surfaces 16, 18 profiled to correspond with the profile of any bone material to which they are to be secured. A pair of sidewalls 20 extends between the upper and lower surfaces 16, 18 and connects to the first end 12 and second end 14. The spinal implant 10 may include at least one opening, cavity, or lumen 24 extending between the upper and lower surfaces 16, 18 to facilitate bony ingrowth or fusion between adjacent bone segments, such as vertebral bodies 2, 4 (not shown in FIG. 1, see FIG. 3B). The cavity 24 may be used to receive and hold a biologically active material, such as a bone graft material or a bone morphogenic protein ("BMP").

As shown, the interbody device 10 may include a tool engaging opening 26. The tool engaging opening 26 may be configured with various shapes and engagement surfaces. For example, the opening 26 may be hexagonal or round with internal threads. The opening 26 is configured to receive an implant delivery tool (not shown in FIG. 1) having a tip with a complimentary shape. Such tools are known to those skilled in the art.

FIG. 2A shows a top plan view of the implant 10 without a protective cover. Once the implant 10 is deployed, for example, into a lumbar disc space in a patient's body (e.g., see FIGS. 3A and 3B), the tool engaging hole 26 is typically left open or exposed. This allows undesired leakage of material 40 from cavity 24 into the surrounding tissue. For example, when used with BMP, the biologic molecules may leak from cavity 24 into the surrounding iliopsoas muscle. While BMP has been shown to be effective in accelerating bone ingrowth, the material is highly inflammatory. Release of the material into that corridor in the lumbar disc near where the interbody fusion device resides, i.e., the iliopsoas muscle, can lead to thigh dysesthesias, numbness, pain, weakness, inflammation, flexion contractures, etc.

Accordingly, FIG. 2B shows a top plan exploded view of the implant 10 with an exemplary embodiment of a protective cover 50 of the present disclosure. As shown, the protective cover 50 may comprise a plate 52 and engagement stem 54. The protective cover 50 may be sized and shaped to compliment the first end 12 and nest securely against the implant 10 in situ when attached. For example, the protective cover 50 may be a generally flat plate of various shapes, such as rectangular, round, oval, etc. The plate 52 is configured to mate with an outer surface of the implant. In other embodiments, the protective cover 50 may have a shaped profile, such as rounded or curved profile. The plate 52 may be constructed from various materials, such as medical-grade metal or polymeric material. In one embodiment, the plate 52 is constructed from PEEK. The plate 52 may be the same or different material as the implant 10.

The engagement stem 54 provides an attaching structure for engaging the protective cover 50 to the implant 10. The engagement stem 54 may attach to the opening by a threaded connection, a snap-fit connection, a press-fit connection, an interference fit, and the like. In one embodiment, the engagement stem 54 is a threaded shaft that can be screwed into tool engaging opening 26. The engagement stem 54 may also be shaped to mate with a corresponding shape, such as hexagon, for opening 26. Furthermore, the protective cover 50 may comprise multiple engagement stems or structures in other embodiments. The engagement stem 54 may be constructed from the same material as the plate.

The protective cover 50 may be implemented as one or more components. For example, the plate 52 and stem 54 may be an integrated unitary body. Alternatively, the plate 52 and stem 54 may be provided as separate components.

FIG. 3A shows a top plan view of the implant 10 and FIG. 3B shows a side view of the implant 10 in situ within a patient's body. As shown, the implant 10 may be lateral interbody fusion device that utilizes a corridor in the lumbar disc space of a patient's body between vertebral bodies 2, 4. As also shown, the implant 10 may hold biologic material in cavity 24. This material may be biologically active, such as in the case of recombinant proteins like BMP-2. In this embodiment, the protective cover 50 is attached to the implant 10, and thus, prevents undesired leakage of material from cavity 24 via opening 26, for example, into the surrounding iliopsoas space around vertebral bodies 2, 4. Accordingly, the material in cavity 24 has a controlled exposure and bony ingrowth has a desired directionality. Of course, the protective cover 50 may also be used to prevent the leakage of other fluids, such as blood or serum, into the iliopsoas space.

FIG. 4 shows another exemplary embodiment of an implantable system including protective cover for the implant 10. In this embodiment, the protective cover 50' may comprise similar features as cover 50. In particular, the protective cover 50' may also comprise a plate 52 and engagement stem 54. The protective cover 50' may be constructed from various materials, such as medical-grade metal or polymeric material.

In addition, the protective cover 50' may comprise lateral structures, such as lateral wings 56. Such structures may provide an additional level of protection for the implant 10 and better conform the cover 50' in situ.

FIG. 5 shows still another exemplary embodiment of a protective cover 70 that may be used with implant 10. As illustrated, the protective cover 70 may comprise a main body 72 having a plate-like configuration extending into lateral wings 74. The lateral wings 74 may extend into and terminate into clips 76. The protective cover 70 may be placed over the tool engaging opening 26 of the implant 10 in the same manner as previously described. However, rather than being threadedly engaged with the implant 10, the protective cover 70 may be snapped onto the implant 10.

In use, the protective cover 70 may be applied onto the implant 10 after implantation, and after placement of the bone graft material or biologically active material within the implant 10. Of course, it is understood that the bone graft material or biologically active material may be contained within the implant 10 prior to implantation, i.e., the implant with the material is implanted together, or the bone graft or biologically active material may be placed into the implant 10 afterwards. Thereafter, the protective cover 70 may be secured to the implant 10 in the manner described hereinabove, in order to block seepage of the material out of the implant 10. In some situations, the protective cover 70 may be removed from the implant 10 after some time, or the protective cover 70 may remain intact.

The description of the invention is provided to enable any person skilled in the art to practice the various embodiments described herein. While the present invention has been particularly described with reference to the various figures and embodiments, it should be understood that these are for illustration purposes only and should not be taken as limiting the scope of the invention.

There may be many other ways to implement the invention. Various functions and elements described herein may be partitioned differently from those shown without departing from the spirit and scope of the invention. Various modifications to these embodiments will be readily apparent to those skilled in the art, and generic principles defined herein may be applied to other embodiments. Thus, many changes and modifications may be made to the invention, by one having ordinary skill in the art, without departing from the spirit and scope of the invention.

A reference to an element in the singular is not intended to mean "one and only one" unless specifically stated, but rather "one or more." The term "some" refers to one or more. Underlined and/or italicized headings and subheadings are used for convenience only, do not limit the invention, and are not referred to in connection with the interpretation of the description of the invention. All structural and functional equivalents to the elements of the various embodiments of the invention described throughout this disclosure that are known or later come to be known to those of ordinary skill in the art are expressly incorporated herein by reference and intended to be encompassed by the invention. Moreover, nothing disclosed herein is intended to be dedicated to the public regardless of whether such disclosure is explicitly recited in the above description.

What is claimed is:

1. An implantable interbody fusion system comprising:
   a lateral interbody device comprising a non-tapered first end, a second end, upper and lower surfaces for placement against vertebral bodies and defining a height profile of the device, a pair of sidewalls extending between the upper and lower surfaces and connecting the first end and second end, at least one cavity between the upper and lower surfaces configured to hold a biologic material that facilitates bony ingrowth between the adjacent vertebral bodies, and an insertion tool engaging opening at the first end, the insertion tool engaging opening being in fluid communication with the at least one cavity; and
   a protective cover configured to prevent leakage of the biologic material from the cavity, wherein the protective cover comprises a plate and at least one stem configured for attachment to the insertion tool engaging opening at the first end, the protective cover being sized and shaped to complement and nest against the first end of the device to block the insertion tool engaging opening and prevent migration of the biological material out of the insertion tool engaging opening, further wherein the protective cover does not extend beyond the height profile of the device.

2. The system of claim 1, wherein the at least one stem attaches to the tool engaging opening by a threaded connection.

3. The system of claim 1, wherein the at least one stem attaches to the tool engaging opening by a press-fit connection.

4. The system of claim 1, wherein the at least one stem attaches to the tool engaging opening by a snap-fit connection.

5. The system of claim 1, wherein the protective cover comprises one or more lateral wings.

6. The system of claim 1, wherein the protective cover comprises a curved profile.

7. The system of claim 1, wherein the protective cover comprises a flat profile.

8. The system of claim 1, wherein the tool engaging opening comprises a hexagonal opening.

9. The system of claim 8, wherein the at least one stem comprises a hexagonal shape that is keyed to the hexagonal opening.

* * * * *